United States Patent
Bystricky et al.

(10) Patent No.: US 11,819,077 B2
(45) Date of Patent: Nov. 21, 2023

(54) SELF-STERILIZING FABRIC FOR PERSONAL PROTECTION AGAINST PATHOGENS

(71) Applicant: American Boronite Corporation, Burlington, MA (US)

(72) Inventors: Pavel Bystricky, Lexington, MA (US); Iva C. Kalus-Bystricky, Lexington, MA (US); David S. Lashmore, Lebanon, NH (US)

(73) Assignee: American Boronite Corporation, Burlington, MA (US)

( * ) Notice: Subject to any disclaimer, the term of this patent is extended or adjusted under 35 U.S.C. 154(b) by 398 days.

(21) Appl. No.: 17/232,839

(22) Filed: Apr. 16, 2021

(65) Prior Publication Data

US 2021/0321703 A1     Oct. 21, 2021

Related U.S. Application Data

(60) Provisional application No. 63/011,256, filed on Apr. 16, 2020.

(51) Int. Cl.
  *A41D 31/30*     (2019.01)
  *A41D 13/11*     (2006.01)
  (Continued)

(52) U.S. Cl.
  CPC ........ *A41D 31/305* (2019.02); *A41D 13/1192* (2013.01); *B32B 5/022* (2013.01);
  (Continued)

(58) Field of Classification Search
  CPC . A41D 31/305; A41D 13/1192; D06M 16/00; D06M 2101/40; B32B 5/022; B32B 5/266; B32B 2262/105; B32B 2262/106
  See application file for complete search history.

(56) References Cited

U.S. PATENT DOCUMENTS 9,198,232 B2    11/2015  Lashmore et al.
10,757,988 B1 *  9/2020  Swogger ............... A61M 16/06
(Continued)

FOREIGN PATENT DOCUMENTS

CA    3105937 A1  *  7/2022
TW    1741709 B   * 10/2021

OTHER PUBLICATIONS

Lee et al., "Carbon Nanotube Mask Filters and Their Hydrophobic Barrier and Hyperthermic Antiviral Effects on SARS-CoV-2," ACS Appl. Nano Mater (Jul. 21, 2021). (Year: 2021).*

(Continued)

*Primary Examiner* — Jeremy R Pierce
(74) *Attorney, Agent, or Firm* — Hamilton, Brook, Smith & Reynolds, P.C.

(57) ABSTRACT

A fabric containing nanotubes which is impervious to viruses, bacteria, and other pathogens; which is self-sterilizing and reusable; and a method of producing the same are disclosed. The fabric can be used to construct facemasks, gloves, protective suits, protective habitats, continuous air filtration/sterilization systems or any other type of protective clothing or structure. The fabric may have integrated temperature monitoring sensors. The fabric may be made into patches which may be integrated into existing articles of clothing. When connected to an electrical power source, either via built-in electrical connections or by induction, the active layer which is one of the components of the fabric will heat to a temperature high enough to eliminate potential biological contamination from viruses, bacteria and other microbial threats. Combining the CNT active layer with an insulating layer will allow a garment to be continuously worn or used without needing removal during multiple sterilization cycles.

20 Claims, 3 Drawing Sheets

(51) Int. Cl.
  *D06M 16/00* (2006.01)
  *B32B 5/02* (2006.01)
  *D06M 101/40* (2006.01)
  *B32B 5/26* (2006.01)

(52) U.S. Cl.
  CPC ............ *D06M 16/00* (2013.01); *B32B 5/266* (2021.05); *B32B 2262/105* (2013.01); *B32B 2262/106* (2013.01); *D06M 2101/40* (2013.01)

(56) References Cited

U.S. PATENT DOCUMENTS

2016/0016022 A1* 1/2016 Qian .................... A62B 23/025
  128/206.12
2021/0307428 A1* 10/2021 Zhamu ............... B01D 39/1615
2022/0265874 A1* 8/2022 Kobrin ................... A61L 2/085

OTHER PUBLICATIONS

English translation to Taiwanese Patent No. 1,741,709 B to Qian et al. (Year: 2021).*

Chad D. Vecitis, et al., "Electrochemical Multiwalled Carbon Nanotube Filter for Viral and Bacterial Removal and Inactivation," Environ. Sci. Technol. 2011, 45, 8, 3672-3679, Mar. 9, 2011.

* cited by examiner

SELF-STERILIZING FABRIC FOR PERSONAL PROTECTION AGAINST PATHOGENS

RELATED APPLICATION

This application claims the benefit of U.S. Provisional Application No. 63/011,256, filed on Apr. 16, 2020. The entire teachings of the above application are incorporated herein by reference.

BACKGROUND

The difficulty in responding to the current COVID-19 pandemic has highlighted the importance of personal protective equipment (PPE). Face masks have to be discarded or removed for sterilization, and even then, only a limited number of cycles are possible before they degrade. Shortages of PPE, and in particular of protective facemasks, gloves, and gowns, stem from a lack of preparedness for a pandemic on such a global scale. Availability of PPE which can be sterilized in a matter of seconds and reused immediately would contribute significantly toward alleviating such shortages. Continuous use PPE would also mitigate the need for hazardous waste logistics and disposal infrastructure required to manage post-use PPE and dramatically improve security for aircraft pilots, train operators, police, medical workers, food handlers, or combat personnel.

SUMMARY

Recent advances in the development and production of conductive very high temperature textiles now make it possible to create fabrics which go beyond traditional clothing and add multiple functionalities such as, for example, protection against biohazard, thermal management, radiation protection, self-sterilization, light weight, high strength, and even the ability to block viruses and transpire water vapor so the wearer will be less fatigued, more comfortable, and safe.

An embodiment according to the present invention is a self-sterilizing fabric comprising: an active layer comprising carbon nanotubes packed to a degree of closeness such that the active layer is both (a) impermeable to a biological threat and (b) allowing at least one of respiration and perspiration of a wearer of the self-sterilizing fabric comprising the active layer; and the active layer being configured to be self-sterilized via generation of internal heat sufficient to destroy biological activity of the biological threat.

In further, related embodiments, the biological threat may comprise at least one of a virus, a bacteria, and a fungus, or another pathogen. The fungus may, for example, comprise a yeast. The virus may, for example, comprise a coronavirus, such as the COVID-19 virus; and may comprise a viral hemorrhagic fever, such as an Ebola virus. The self-sterilizing fabric may further comprise at least one inner or outer protection layer; and may further comprise at least one internal layer configured to provide at least one of: skin-contact protection, thermal protection, radiation protection (including, for example, microwave protection), and ballistics protection. The self-sterilizing fabric may be configured to be rapidly self-sterilized via the generation of internal heat. The carbon nanotubes may comprise nonwoven carbon nanotubes. The non-woven carbon nanotubes may be condensed with a solvent. The self-sterilizing fabric may be continuously worn or used without needing removing or replacing during multiple sterilization cycles. The self-sterilizing fabric may further comprise at least one internal layer configured to provide self-sterilization when removed from wear, thereby enabling reuse and sharing among wearers or users. The self-sterilizing fabric may be configured to be removed and both an internal and an external layer sterilized, thereby allowing for transfer and use by another wearer or user.

Another embodiment is an item of protective equipment comprising any of the self-sterilizing fabrics taught herein. The item of protective equipment may comprise personal protective equipment (PPE) or a protective structure; and may comprise at least one of: a facemask, a face shield, a hair net, a glove, a vest, pants, a full bodysuit, a flight suit, a tent, a habitation, a filter and other articles of protective clothing and structures.

Another embodiment is an item of personal protective equipment comprising a layered system comprising: a thermal insulating layer configured to be placed between the CNT layer and a person's body; a CNT non-woven textile configured to block a biological threat and to transpire water and air; and a protective outer layer.

In further, related embodiments, the biological threat may comprise a virus. The item may further comprise a radiation protection layer of BNNTs. The item may further comprise any of the self-sterilizing fabrics taught herein.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

Figure 1:
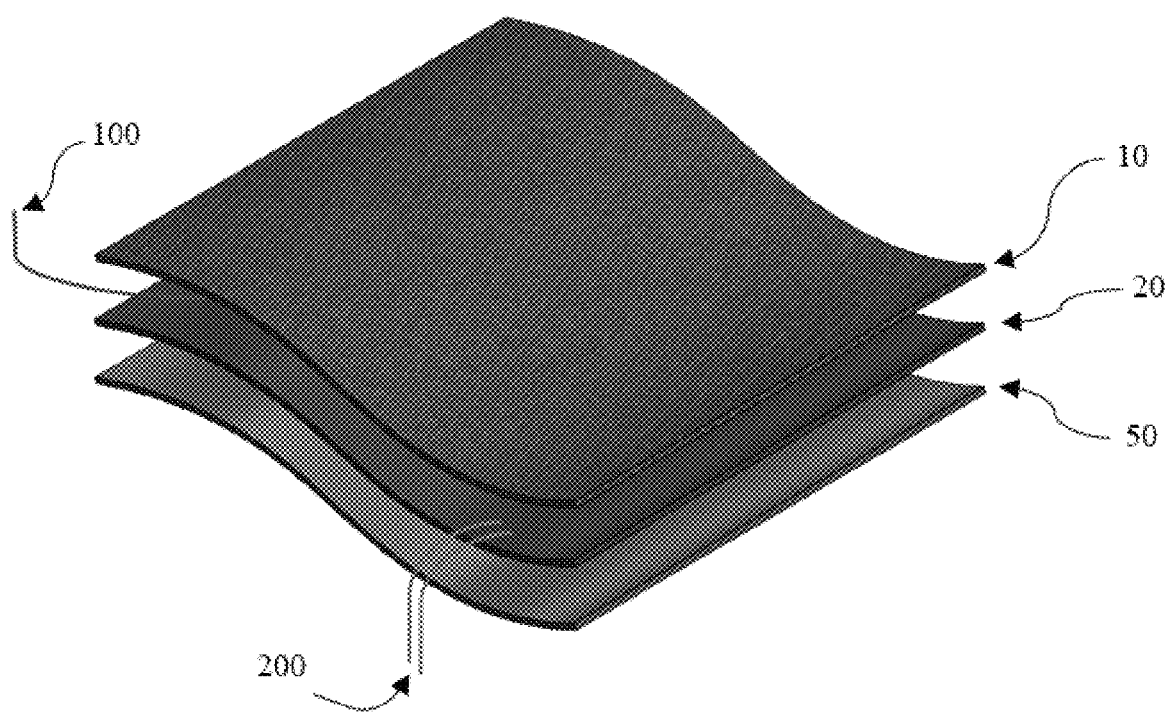
FIG. 1 is a schematic diagram of a self-sterilizing layered fabric structure, in accordance with an embodiment of the invention.

A description of example embodiments follows.

A fabric containing nanotubes which is impervious to viruses, bacteria, and other pathogens; which is self-sterilizing and reusable; and a method of producing the same are disclosed. The fabric can, for example, be referred to as "Sterilayer™" herein. The fabric can be used to construct facemasks, gloves, protective suits, protective habitats, continuous air filtration/sterilization systems or any other type of protective clothing or structure. The fabric may have integrated temperature monitoring sensors. The fabric may be made into patches which may be integrated into existing articles of clothing. When connected to an electrical power source, either via built-in electrical connections or by induction, the active layer which is one of the components of the fabric will heat to a temperature high enough to eliminate potential biological contamination from viruses, bacteria and other microbial threats. Most pathogens typically cannot survive temperatures above 130° C., so heating to 150° C. for very short times should destroy all pathogens. Combining the CNT active layer with an insulating layer (such as an aerogel or boron nitride nanotube (BNNT) layer) will allow a garment such as a protective coat, clean room suit, flight suit, glove or vest to be continuously worn or used without needing removal during multiple sterilization cycles. Optionally, an integrated battery may be used for field use where access to an external power source would be difficult.

Layers of carbon nanotube (CNT) non-woven fabric condensed into sheets have been shown (see Reference (1)) to be impermeable to the passage of small pathogens, such as viruses, bacteria, yeasts and fungi, while remaining breathable. Furthermore, when a current is applied to such a CNT sheet, resistive heating allows it to be heated rapidly to a desired temperature. When current is removed, the CNT sheet will cool down very fast. Very rapid changes in temperature in this material are made possible by its low heat capacity. A multilayer Sterilayer™ fabric containing a CNT filtering layer on the outside (exterior facing) and at least one layer such as wool on the inside (interior facing)—and other layers such as an external protective layer and an internal insulating layer such as a BNNT layer or an aerogel—can therefore be heated rapidly (to 100 to 200° C., preferably 150° C., for example) by applying current in order to destroy any potential biological function of pathogens present on the exterior surface of the material in seconds (10 to 60 s, preferably less than 10 s or less than 1 s). Here, "rapidly" means within less than 1 to 60 seconds, and can be within less than 10 seconds, such as within less than 1 second. Sensors inside and out may be used to measure the environment, monitor temperature and manage heating rates. Systemic savings of this approach include dramatic simplification and reduction of PPE stockpiling and supply chains, reduction in critical staff downtime, simplification and reduction of waste logistics, the substitution and elimination of multiple other materials and processes.

Figure 2:
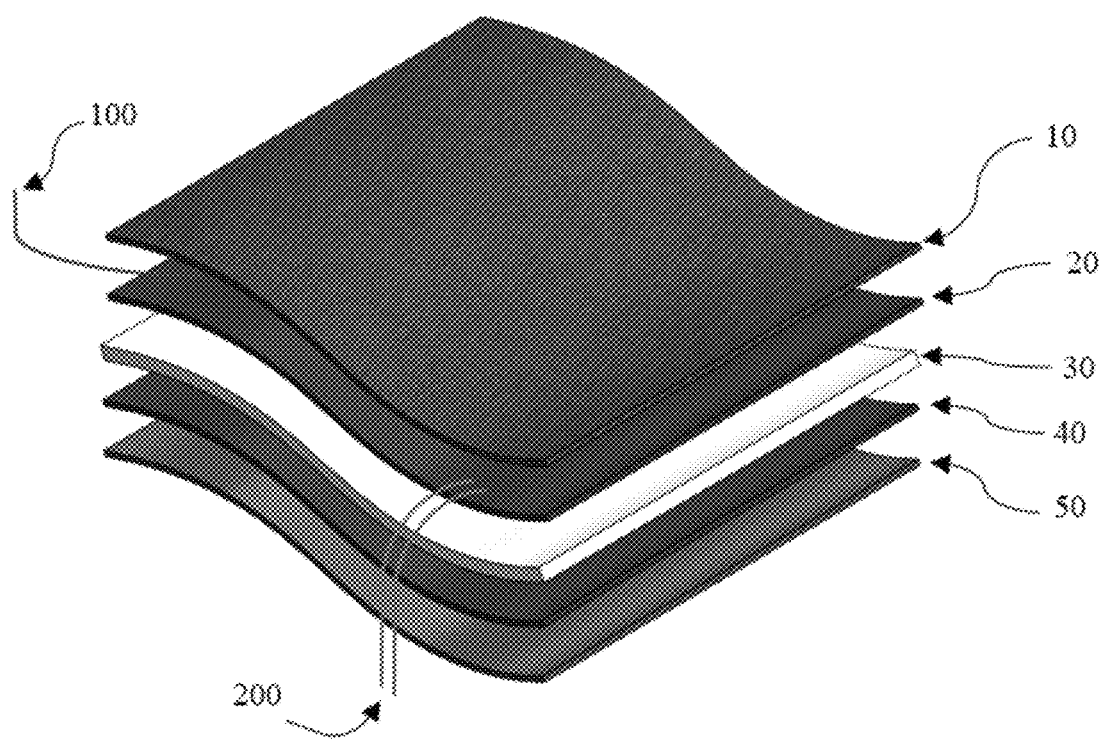
FIG. 2 is a schematic diagram of a self-sterilizing layered fabric structure, in accordance with another embodiment of the invention.

In an embodiment, the self-sterilizing Sterilayer™ fabric is a closely packed layer of non-woven CNTs, also called an active layer, which in FIGS. 1 and 2 is represented by either layer 10, or layer 20, or a combination of layer 10 and layer 20. A temperature monitoring device is embedded within the structure in contact with the active layer such that temperature may be monitored during cleaning/sterilizing and overheating may be prevented. Optionally, electrical connections may also be made to the active layer for applying a current used to heat the material to sterilize it. Alternative to direct electrical connections, heating of the active layer may also be achieved by induction. In this latter case, the fabric may be placed in close proximity to a power source which, when turned on, will induce a current within the CNT network, allowing resistive heating to sterilize the fabric. This power source may be alternating current (AC) or direct current (DC) in the case of direct electrical connections or AC only for induction. Optionally there may be a copper strip deposited along one or more layers to distribute applied current distribution uniformly and therefore to reduce hot spots. Optionally, the Sterilayer™ fabric may be fitted with an integrated battery to allow self-sterilization in the field where access to an external power source may be limited.

The active CNT layer of the Sterilayer™ fabric may be made from non-woven tangled nanotubes produced by chemical vapor deposition (CVD) and collected on a spool, between paper strips or on a belt or cylinder. The process to produce yarns or sheets involves a gas phase pyrolysis of a proprietary organic carbon source such as ethanol, ethylene or toluene. These organic chemicals are introduced into a CVD reactor through a series of temperature gradients designed to establish the diameter of the catalysts and initiate nanotube growth on the catalyst particles, typically iron. As the nanotubes proceed down the reactor, they form a hollow structure held together by electrostatic interactions. This structure, or "sock", facilitates the stretching and alignment of the tubes during the sheet collection or yarn formation process. As the sock exits the reactor it can be collected in sheet form on a spool or guided into a textile yarn formation system which stretches and aligns the material, spins it to create a twist, and rolls up the now formed and completed yarn in one step on a bobbin. When such a CNT fabric is treated with a solvent, the nanotubes condense into tightly packed sheets which allow air or water vapor through, but which are impermeable to the passage of small biological agents, such as viruses and bacteria. Alignment of the nanotubes can serve to reduce the voltage requirements and therefore reduce EMI emission during the heating cycle.

FIGS. 1 and 2 present schematically two embodiments of the Sterilayer™ fabric's multilayered structure. Components of the fabric, including layers shown separated for clarity from top (exterior facing) to bottom (skin contact or interior facing), include:

An outer layer 10
A single middle layer 20 or multiple middle layers, for example 20, 30, 40.
An inner layer 50
A temperature monitoring device 100 such as, for example, a thermocouple, embedded between layer 10 and layer 20.

Optionally, electrical leads 200 attached to layer 10 and/or layer 20. Leads may be attached by crimping, soldering, or another method which will allow electrical contact between the conductors and the CNT network. Electrical leads 200 are represented schematically as relatively close together for clarity. In practice, separating the leads by a greater distance (up to, for example, extreme ends of the active layer) would be preferred to allow more uniform heating of the active layer. Copper or silver electrodes may be added to create a uniform current density.

Inner layer 50 may be made for example of wool or another material which is temperature resistant and compatible with skin contact. This includes, for example, a stretchable modified polyurethane fabric (such as, for example, the polyether-polyurea copolymer used to manufacture Spandex) which may be specially formulated to withstand short term temperatures up to 150° C. that will allow the PPE material to be heated for sterilization. When the PPE fabric is used for face protection, the skin-contacting surface of inner layer 50 may be supplemented with a disposable insert such as a paper filter or a disposable surgical facemask.

The active layer (layer 10, or layer 20, and/or a combination of layer 10 and layer 20) is composed of a network of closely packed CNTs, either as a non-woven CNT fabric which may be condensed by wetting with a solvent, or as a woven or knitted fabric made from spun CNT yarn. Where a solvent is used, it can, for example, be or include one or more of acetone, isopropyl alcohol, ethanol, or another suitable high vapor pressure liquid. Outer layer 10 may include a thin, porous, temperature resistant, material for protecting the active CNT material, for example for protection against abrasion. In cases where layer 20 is the active layer, layer 10 can be composed of polyurethane fabric (such as Spandex) or any fabric that can tolerate the temperature (such as wool) or can be specially formulated to withstand short term temperatures to 150° C. or preferably up to 170° C. that will allow the PPE material to be heated for sterilization.

Layers 30 and 40 may optionally add structural integrity and thermal insulation to the PPE fabric. Thermal insulation is useful, for example, to protect the internal layer 50 from the heat generated by thermal self-sterilization of the active layer. Layer 30 may, for example, be composed of boron nitride nanotubes (BNNTs) which are similar in structure to CNTs but are electrically insulating and provide thermal protection. Adding such an insulating layer would have the advantage of potentially allowing the active layer to be heated for cleaning purposes without necessitating removal of the garment by the wearer. In addition, a BNNT layer provides additional protection against harsh environments, including 1) thermal protection against extreme heat and cold and 2) radiation protection. Non-woven CNTs also provide significant thermal protection normal to the plane of the fabric, especially if doped with Boron or the like. A crosslinked aerogel or X-aerogel can also be used. Boron has by far the largest neutron absorption cross section of all elements: $^{11}B$ is 710 barns and $^{10}B$ is 3835 barns, compared to nitrogen (still relatively large at 1.9) and carbon at 0.0035 (Source: NASA publication NP-2011-03-359-LaRC). A BNNT layer therefore provides thermal neutron absorption and can absorb other forms of radiation when loaded with hydrogen or combined with a highly hydrogenated polymer such as polyethylene. The BNNT layer may be of particular advantage for flight suits to reduce radiation exposure to the pilot.

CVD systems can, for example, be used to produce the nanotube material necessary for making the Sterilayer™ active layer.

Figure 3:
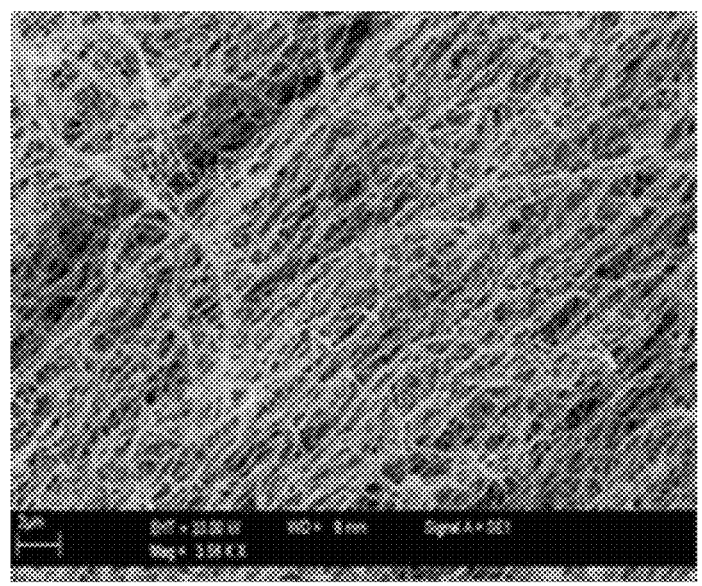
FIG. 3 is an image of nanotube microstructure, prior to condensing, that can be used in a fabric in accordance with an embodiment of the invention.

FIG. 3 is a scanning electron microscope picture of a tangled web of nanotubes manufactured in a CVD system shown as-produced when the material is collected as a non-woven sheet. The material in FIG. 3 is shown before condensing treatment. After the material has been condensed, it may be used as the active layer component of the Sterilayer™. The active layer can, for example, have carbon nanotubes packed to a degree of closeness such that they have openings less than about 300 nm, such as less than about 200 nm, or between about 100 nm and 300 nm, or between about 20 nm and 300 nm. The degree of closeness can be selected to obtain a desired level of permeability, for example to permit one or more of respiration or perspiration, depending on the end use of the fabric. In some embodiments, the active layer need not have such small openings, but can achieve similar results by using multiple layers of carbon nanotubes, or by having a sufficient thickness of carbon nanotube materials.

Definitions

As used herein, a "carbon nanotube" (or "CNT") can be thought of as a graphene plane rolled up into a tube capped with a half of a Bucky sphere at one end and usually a magnetic transition metal catalyst at the other. This graphene plane is characterized by $sp^2$ hybridized bonding which gives the surface its hexagonal symmetry, very good electronic properties, high strength, and a modulus of about 1 TPa and a unique Raman spectrum. These properties clearly distinguish CNTs from carbon fibers. Carbon nanotubes have a diameter range from about 0.8 nm to over 100 nm, typically ranging from about 1 to 10 nm. The length of these tubes spans from a few microns to many millimeters and occasionally to 20 or more centimeters. More typically they are about 1 or 2 millimeters in length. The tubes can be a single wall of graphene or dual wall or multiwalls. Very small diameter tubes, say less than 5 nm, are typically single walls. Depending on their structure (diameter and graphene plane configuration) they can conduct electricity as a metal or a semiconductor. They are black.

As used herein, a "boron nitride nanotube" (or "BNNT") is a well-ordered structure of alternating $sp^2$ hybridized boron and nitrogen atoms forming a hexagonal plane rolled up into a tube. They are electrical insulators, possess piezoelectric characteristics, have high strength, and a modulus somewhat less than 1 TPa. The boron atoms in their structure makes BNNTs excellent absorbers of neutron radiation. They are white.

As used herein, a "tape" or "continuous nanotube tape" is usually a non-woven structure of nanotubes held together by electrostatic forces and by entanglement between the tubes. It can be produced in situ during growth or be cut from a large sheet and be bonded together with an adhesive to produce a continuous structure. The width of a tape can run from 0.5 cm to about 10 cm, its thickness can range from about 2 microns to about 200 microns, typically about 50 microns. Alternatively, tapes can be woven from aligned yarns.

As used herein, a "sheet" or "continuous nanotube sheet" is a wide tape produced in a batch system and bonded to another tape to constitute a continuous sheet (thousands of feet long) or it can be produced on a machine in a continuous manner. These structures are typically non-woven, their width ranges from about 10 cm to about 500 cm, their thickness ranges from about 2 microns to about 200 microns. Alternatively, continuous nanotube sheet or fabric can be woven from nanotube yarns in a manner known to the textile industry.

REFERENCE (1) *Environ. Sci. Technol.* 2011, 45, 8, 3672-3679, Mar. 9, 2011, https://doi.org/10.1021/es2000062.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A self-sterilizing fabric comprising:
   an active layer comprising carbon nanotubes packed to a degree of closeness such that the active layer is both (a) impermeable to a biological threat and (b) allowing at least one of respiration and perspiration of a wearer of the self-sterilizing fabric comprising the active layer; and
   the active layer being configured to be self-sterilized via generation of internal heat sufficient to destroy biological activity of the biological threat.

2. The self-sterilizing fabric of claim 1, wherein the biological threat comprises at least one of a virus, a bacteria, and a fungus.

3. The self-sterilizing fabric of claim 2, wherein the virus comprises a coronavirus.

4. The self-sterilizing fabric of claim 3, wherein the virus comprises a COVID-19 virus.

5. The self-sterilizing fabric of claim 2, wherein the virus comprises a viral hemorrhagic fever.

6. The self-sterilizing fabric of claim 2, wherein the fungus comprises a yeast.

7. The self-sterilizing fabric of claim 1, further comprising at least one inner or outer protection layer.

8. The self-sterilizing fabric of claim 1, further comprising at least one internal layer configured to provide at least one of: skin-contact protection, thermal protection, radiation protection, and ballistics protection.

9. The self-sterilizing fabric of claim 1, configured to be rapidly self-sterilized via the generation of internal heat.

10. The self-sterilizing fabric of claim 1, wherein the carbon nanotubes comprise nonwoven carbon nanotubes.

11. The self-sterilizing fabric of claim 10, wherein the nonwoven carbon nanotubes are condensed with a solvent.

12. The self-sterilizing fabric of claim 1, wherein the self-sterilizing fabric can be continuously worn or used without needing removing or replacing during multiple sterilization cycles.

13. The self-sterilizing fabric of claim 1, further comprising at least one internal layer configured to provide self-sterilization when removed from wear, thereby enabling reuse and sharing among wearers or users.

14. The self-sterilizing fabric of claim 1, wherein the self-sterilizing fabric is configured to be removed and both an internal and an external layer sterilized, thereby allowing for transfer and use by another wearer or user.

15. An item of protective equipment comprising a self-sterilizing fabric, the self-sterilizing fabric comprising:
   an active layer comprising carbon nanotubes packed to a degree of closeness such that the active layer is both (a) impermeable to a biological threat and (b) allowing at least one of respiration and perspiration of a wearer of the self-sterilizing fabric comprising the active layer; and
   the active layer being configured to be self-sterilized via generation of internal heat sufficient to destroy biological activity of the biological threat.

16. The item of protective equipment of claim 15, comprising personal protective equipment (PPE) or a protective structure.

17. The item of protective equipment of claim 15, comprising at least one of: a facemask, a face shield, a hair net, a glove, a vest, pants, a full bodysuit, a flight suit, a tent, a habitation, a filter, and other articles of protective clothing and structures.

18. An item of personal protective equipment comprising a layered system comprising:
   a thermal insulating layer configured to be placed between a carbon nanotube (CNT) layer and a person's body;
   a carbon nanotube (CNT) non-woven textile configured to block a biological threat and to transpire water and air;
   a self-sterilizing fabric comprising an active layer comprising carbon nanotubes packed to a degree of closeness such that the active layer is both (a) impermeable to a biological threat and (b) allowing at least one of respiration and perspiration of a wearer of the self-sterilizing fabric comprising the active layer, wherein the active layer is configured to be self-sterilized via generation of internal heat sufficient to destroy biological activity of the biological threat; and
   a protective outer layer.

19. The item of claim 18, wherein the biological threat comprises a virus.

20. The item of claim 18, further comprising a radiation protection layer of boron nitride nanotubes (BNNTs).

* * * * *